United States Patent [19]

Epstein et al.

[11] Patent Number: 5,549,689
[45] Date of Patent: Aug. 27, 1996

[54] PROSTHETIC KNEE

[76] Inventors: Norman Epstein, Rte. No. 301, Carmel, N.Y. 10512; Steven B. Zelicof, 12 Seneca Rd., Scarsdale, N.Y. 10583

[21] Appl. No.: 345,472

[22] Filed: Nov. 28, 1994

[51] Int. Cl.⁶ .................................................. A61F 2/38
[52] U.S. Cl. ................................................ 623/20; 623/18
[58] Field of Search .................................. 623/20, 18, 22

[56] References Cited

U.S. PATENT DOCUMENTS

| | | | |
|---|---|---|---|
| 4,262,368 | 4/1981 | Lacey . | |
| 4,301,553 | 11/1981 | Noiles | 623/20 |
| 4,358,859 | 11/1982 | Schurman et al. . | |
| 4,673,408 | 6/1987 | Grobbelaar | 623/20 |
| 4,865,606 | 9/1989 | Rehder | 623/20 |
| 4,919,660 | 4/1990 | Peilloud | 623/20 |
| 5,037,439 | 8/1991 | Albrektsson et al. | 623/20 |
| 5,116,375 | 5/1992 | Hofmann | 623/20 |
| 5,139,521 | 8/1992 | Schelhas | 623/20 |
| 5,147,406 | 9/1992 | Houston et al. | 623/20 |
| 5,176,684 | 1/1993 | Ferrante et al. | 606/86 |
| 5,197,986 | 3/1993 | Mikhail | 623/20 |
| 5,197,987 | 3/1993 | Koch et al. | 623/20 |
| 5,282,867 | 2/1994 | Mikhail | 623/20 |
| 5,314,480 | 5/1994 | Elloy et al. | 623/20 |
| 5,314,481 | 5/1994 | Bianco | 623/20 |
| 5,413,607 | 5/1995 | Engelbrecht et al. | 623/20 |
| 5,413,608 | 5/1995 | Keller | 623/20 |

FOREIGN PATENT DOCUMENTS

| | | | |
|---|---|---|---|
| 0472475 | 2/1992 | European Pat. Off. | 623/20 |
| 2277034 | 10/1994 | United Kingdom | 623/20 |
| 9421198 | 9/1994 | WIPO | 623/20 |

*Primary Examiner*—David H. Willse
*Assistant Examiner*—Bruce E. Snow
*Attorney, Agent, or Firm*—Parmelee, Bollinger & Bramblett

[57] ABSTRACT

An artificial knee joint is provided in which a femoral component, a tibial component and a patella component simulate all the movements of a natural knee utilizing movable bearings between such components and elements thereof. In addition, a portion of the joint for flexion and extension may be repaired without involving major reconstructive surgery.

6 Claims, 2 Drawing Sheets

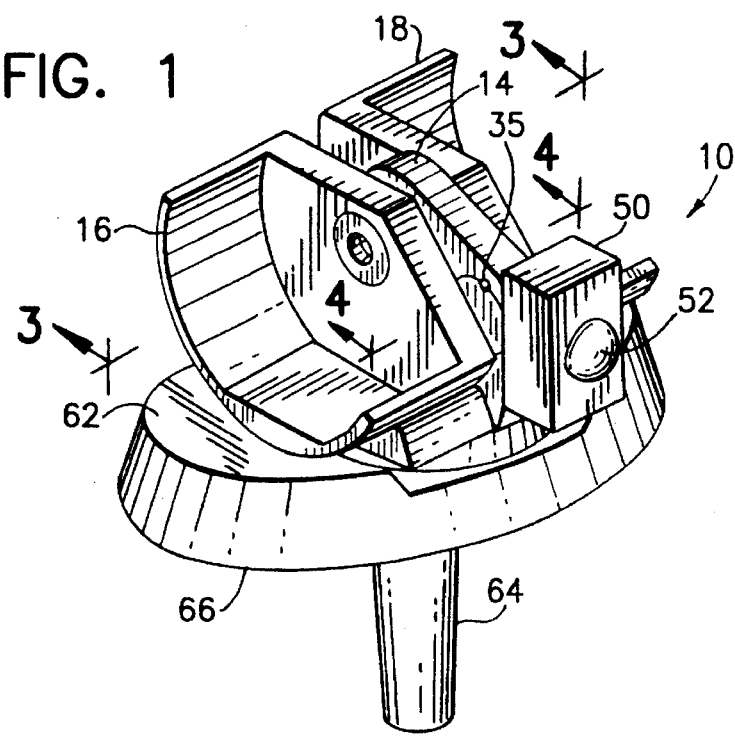
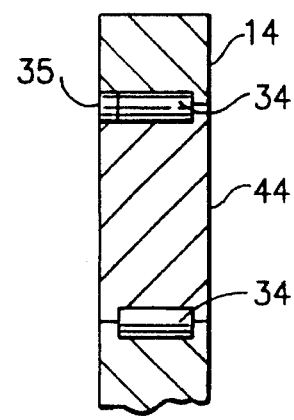
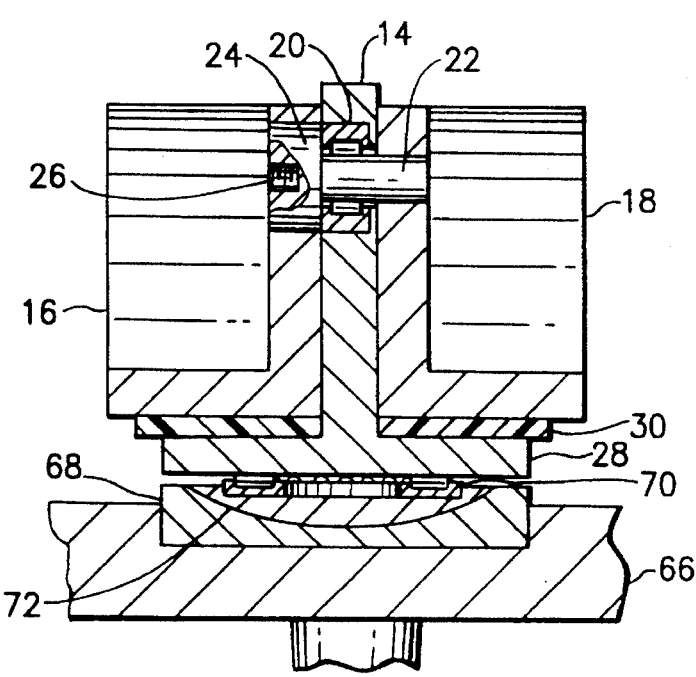
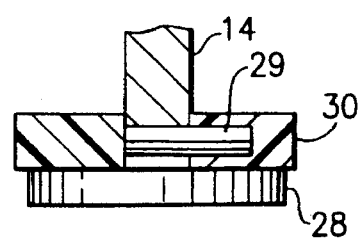

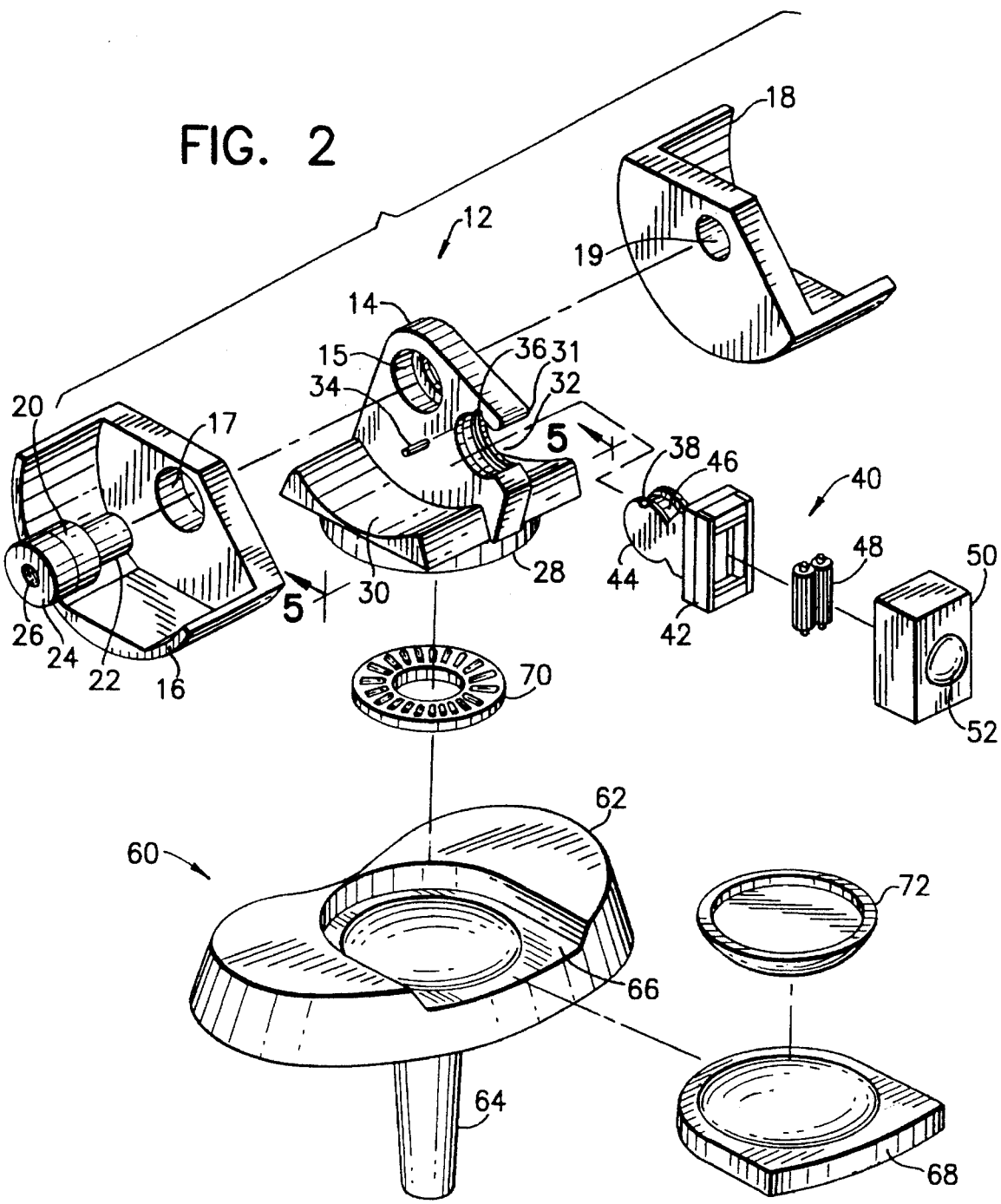

PROSTHETIC KNEE

BACKGROUND OF THE INVENTION

This invention relates to prosthetic knee joints, and more particularly to improved prosthetic knee joints, which emulate the operation of a normal knee with little friction for prolonging the life of the artificial knee.

Conventional movement in a healthy human knee joint involves complex movements of the femur, the tibia, and the patella. In flexion, the distal end of the femur and the proximal end of the tibia rotate and glide relative to one another with the center of rotation of the joint moving posteriorly over the condyles of the femur. In extension, the reverse of the aforesaid movement takes place. Simultaneously therewith, the patella or kneecap moves over the femoral condyles while remaining at a relatively constant distance from the tubercle of the tibia via the patella ligament attached to the patella.

Numerous attempts have been made to produce prosthetic knee joints which emulate the complex aforesaid knee function with somewhat limited success. The proposed joints with their contact and bearing surfaces produce restricted movements, suffer from wear and tear, shed debris, provide improper support of the bones involved causing bone deterioration, wear out, etc. Probably the biggest drawback of the prosthetic knee joint is that the breakdown of the joint most commonly due to bearing surface wear, regardless of the cause, results in the requirement of major surgery to replace the prosthetic joint. Prosthetic knees do not lend themselves to minor surgery for repair or replacement, which is costly and limits their use. The average life of prosthetic knees is ten to fifteen years.

SUMMARY OF THE INVENTION

Accordingly, it is an object of this invention to provide a new and improved prosthetic knee joint having a longer life.

Another object of this invention is to provide a new and improved prosthetic knee joint which is constructed to permit repair or replacement of critical components without requiring major reconstructive surgery.

Still another object of this invention is to provide a new and improved prosthetic knee which eliminates major bearing surfaces, thereby limiting wear and tear as well as the generation of debris from the rubbing between bearing surfaces.

Yet another object of this invention is to provide a new and improved prosthetic knee which maintains similar forces on the femur and tibia bones in the leg as a normal knee in order to prevent deterioration of such bones.

Still another object of this invention is to provide a new and improved prosthetic knee joint which receives the body weight in the same area and permits articulation resembling that of a normal knee with no rubbing.

In carrying out this invention in one illustrative embodiment thereof, a femoral support in a prosthetic knee joint is provided having laterally disposed femoral condyle carriers adapted to receive and hold shaped femoral condyles of the user mounted in said femoral support for movement therein. Roller bearings positioned on a pin extending therethrough are mounted in said femoral support for rotational movement therein. The distal ends of the pin have the condyle carriers of the femoral support mounted for rotational movement thereon. The femoral support has a femoral base which supports the full load on the femur.

BRIEF DESCRIPTION OF THE DRAWINGS

The invention together with further objects, advantages, features and aspects thereof, will be more clearly understood from the following description taken in connection with the accompanying drawings.

FIG. 1 is an assembled perspective view of the prosthetic knee joint of the present invention.

FIG. 2 is an exploded perspective view of the prosthetic knee joint of FIG. 1.

FIG. 3 is a cross-sectional view taken along line 3—3 of FIG. 1.

FIG. 4 is a cross-sectional view taken along line 4—4 of FIG. 1.

FIG. 5 is a cross-sectional view taken along line 5—5 of FIG. 2.

DESCRIPTION OF THE PREFERRED EMBODIMENTS

Repetitive loading bearing activities of the knee joint, which loads are primarily in compression, can generate loads of 2.5 times body weight for walking and 8 times body weight for stair climbing. In addition to direct compressive loading, the knee must be able to provide physiologic flexion of 130 degrees, varus-valgus movements of 10 degrees and axial rotation of 30 degrees. The patellofemoral articulation is also loaded mainly in compression and needs to accommodate the flexion of 130 degrees, axial rotation of 6 degrees and the ability to tilt laterally and medially in the femoral groove without dislocating or rubbing on an edge. Human artificial knee joint replacement has attempted to provide the aforesaid movements without overloading the bearing surfaces, which causes wear in the artificial knee joint, by using more congruent meniscal bearing surfaces. The present invention replaces such bearing surfaces with moveable bearings such as roller or ball bearings, which can handle heavier loads as well as the required movement in the artificial knee joint without exhibiting the wear of presently used plane or curved bearing surfaces.

Referring now to FIGS. 1 and 2, the prosthetic knee, which is referred to generally with the reference numeral 10, comprises three basic components; namely, the femoral component 12, the tibial component 60 and the patella component 40. The femoral component 12 has a femoral support 14 with a mounting hole 15, an arcuate recess 32 adapted to receive for mounting therein a patella component 40. The femoral component 12 has a base 28 carrying the femoral support 14 and a saddle 30 which is mounted in the femoral support 14 with a pin 29 (see FIG. 5).

A pair of condylar carriers 16 and 18 having mounting holes 17 and 19, respectively are mounted for rotational movement on the distal ends of pin 22. As will best be seen in FIG. 3, the pin 22 has a head 24 on one distal end therefor which extends in the mounting hole 17 of condyle carrier 16. The head 22 has a threaded hole 26 therein for facilitating the removal of the pin in case of a breakdown in the joint 10. The pin 22 is mounted on roller bearings 20 in the mounting hole 15 of the femoral support 14. The condyles of the femur of the user are resected to fit in and be secured in the condylar carriers 16 and 18 for pivotal movement along with pin 22 which rotates on roller bearings 20. Such movement simulates flexion and extension of a natural joint. Since the movement of pin 22 takes place on roller bearings, less friction occurs than in artificial joints employing meniscal bearing surfaces. Should trouble or a breakdown of the described joint occur, the mounting pin 22 and roller bearings 20 may be removed by the lateral insertion and engagement of the threaded hole 26 in the head 24 of the pin 22 by a suitable tool for that purpose. Such a repair could be accomplished without requiring major reconstructive knee surgery. In the event of a breakdown, the condyle carriers will come to rest on the saddle 30, which provides a back-up bearing surface until a repair is made.

The patella component 40 includes a patella support member 42 which carries an arcuate extension 44 and has a recessed bearing race 46 therein with a lower half of a keyway 38. The patella support member 42 is mounted on the femoral support 14 by the mounting of arcuate extension 44 in an arcuate recess 32 in femoral support 14. The arcuate recess 32 has an upper half of a keyway 36 therein whereby with the mounting of arcuate extension 44 in the recess 32, mates half keyways 36 and 38 to form a keyway 35 therein. Roller bearings 34 are inserted in the keyway 35 falling into the bearing race 46 which has been enclosed by the femoral support 14. The arcuate recess 32 terminates in stops 31 and 33 on the distal ends of the recess 32 which restricts the up and down pivotal movement of the patella component 40 on the roller bearings 34.

The patella component 40 also includes a patella pivoting section 50 mounted for limited predetermined movement on roller bearings 48 mounted in the patella support member 42. The pivoting section 50 carries a patella pin 52 which is adapted to receive the patella of the user or an artificial patella (not shown).

The patella component thus described provides predetermined limited up and down and side to side movements thereby simulating the movement of a natural patella on a natural knee. These are accomplished using roller bearings to limit the amount of friction generated.

The tibial component 60 comprises a tibial tray 62 carried by a tibial post 64 which is adapted to be embedded in the tibia of the user. The tibial tray 62 includes a tibial socket 66 which is adapted to house a shim 68 or additional shims which in effect provide a knee joint adjustment. A radial thrust bearing 70 is positioned on a plastic liner 72 in the tibial socket 66. The femoral component 12 is mounted on the tibial component 60 with the femoral base positioned on the radial thrust bearing 70 in the tibial socket 66. Accordingly, the femoral component is mounted for a predetermined, limited rotational movement on said tibial component. Again, such movement is based on reduced frictional type engagement with bearings instead of on solid surface contact.

The artificial knee joint described above simulates all of the movements of the natural knee. All such movements are on movable bearings for reducing friction between the contacting elements. In addition, none of the components directly rub, engage or otherwise provide any additional frictional wear. In addition, the major joint for simulating flexion and extension may be repaired without requiring major reconstructive surgery.

Since other modifications and changes varied to fit particular operating requirements and environments will be apparent to those skilled in the art, the invention is not considered limited to the examples chosen for purposes of disclosure and covers all modifications and changes which do not constitute departures from the true spirit and scope of this invention.

What is claimed is:

1. In a prosthetic knee joint for providing movement between at least two bones comprising:

a femoral support having laterally disposed femoral condyle carriers mounted in said femoral support for movement therein adapted to receive and hold resected femoral condyles of a user, roller bearing means carrying a pin mounted in said femoral support for rotational movement therein, to provide low friction articulation of the prosthetic knee joint, said pin extending through said roller bearing means and femoral support, the distal ends of said pin having said condyle carriers mounted thereon for rotational movement therewith, said femoral support having a femoral base thereon which supports the full load on the femur, condyle carriers being spaced from said femoral base to prevent contact therebetween, a patella support, patella support mounting means in said femoral support having roller bearings positioned therein for mounting said patella support in said femoral support and providing a limited up and down rotation of said patella on said roller bearings in said femoral support to limit wear between the patella and femoral supports.

2. In the prosthetic knee joint as claimed in claim 1 wherein said patella support has a pivoting section thereon mounted on roller therefore bearings for right or left motion in said patella support.

3. In the prosthetic knee joint as claimed in claim 2 wherein said pivoting section of said patella support has a pin positioned on the front surface thereof adapted to have the patella of the user mounted thereon for limited radial movement in four directions without rubbing.

4. In the prosthetic knee joint for providing movement between at least two bones comprising:

a femoral support having laterally disposed femoral condyle carriers mounted in said femoral support for movement therein adapted to receive and hold resected femoral condyles of a user, roller bearing means carrying a pin mounted in said femoral support for rotational movement therein to provide low friction articulation of the prosthetic knee joint, said pin extending through said roller bearing means and femoral support, the distal ends of said pin having said condyle carriers mounted thereon for rotational movement therewith, said femoral support having a femoral base thereon which supports the full load on the femur, said condyle carriers being spaced from said femoral base to prevent contact therebetween, a tibial tray and tapered tibial post on the bottom thereof adapted to be embedded in the tibia, a tibial socket positioned in the top of said tibial tray adapted to receive and position said base of said femoral support on said tibial tray and, thrust radial roller bearing means mounted in said socket and interposing said thrust roller bearing means between said femoral base and said tibial tray for providing limited rotational movement of said femoral support on said tibial base plate to minimize wear from repetitive pivotal and rotational loading on said tibial tray, a patella support with a pivoting section, means for mounting said patella support in said femoral support for up and down movement therein in a predetermined range, means for mounting said pivoting section in said patella support for right and left motion therein within a predetermined range.

5. In the prosthetic knee joint as claimed in claim 4 wherein said means for mounting said patella support in said femoral support and said pivoting section in said patella support comprise roller bearing means for limiting friction therefore between the moveable parts of said patella support and said femoral support.

6. In a prosthetic knee joint for emulating the movement of a natural knee joint comprising:

a femoral support with a femoral base thereon, a pair of laterally disposed femoral condyle carriers adapted to house resected femoral condyles of a user, which have the same configuration as said condyle carriers, a pin having said pair of condyle carriers mounted on opposed distal ends of said pin, and when said condyle carriers are mounted on said pin, they are spaced from and out of frictional contact with said femoral base, roller bearing means for mounting said pin for rotational movement in said femoral support, thereby providing simultaneous movement of said condyle carriers and thereby placing the full load on a femur positioned on said femoral support on said femoral base, a tibial tray having atop and bottom with a mounting post extending from the bottom thereof adapted to be embedded in the tibia of the user, thrust radial roller bearing means for mounting said femoral base of said femoral support on the top of said tibial tray for permitting the rotation of said femoral support on said tibial tray and preventing rubbing therebetween, a patella support with a pivoting section, roller bearing means for mounting said patella support in said femoral support to provide a swinging up and down movement therein, roller bearing means for mounting said pivoting section in said patella support for side to side movement therein without rubbing contact, and a pin protruding from said pivoting section of said patella support adapted to mount a patella of the user thereon, thereby providing radial arcuate quadrant movement of the patella positioned thereon.

\* \* \* \* \*